(12) United States Patent
Collins (10) Patent No.: US 8,550,814 B1
(45) Date of Patent: Oct. 8, 2013

(54) MULTI-COMPONENT ORTHODONTIC BRACKET ASSEMBLY

(76) Inventor: Monte Collins, Colleyville, TX (US)

( * ) Notice: Subject to any disclaimer, the term of this patent is extended or adjusted under 35 U.S.C. 154(b) by 0 days.

(21) Appl. No.: 13/586,969

(22) Filed: Aug. 16, 2012

(51) Int. Cl.
*A61C 3/00* (2006.01)
(52) U.S. Cl.
USPC .................................... 433/9; 433/17
(58) Field of Classification Search
USPC .............................. 433/8, 9, 10, 17
See application file for complete search history.

(56) References Cited

U.S. PATENT DOCUMENTS

| | | | |
|---|---|---|---|
| 3,421,221 A * | 1/1969 | Silverman et al. | 433/8 |
| 3,461,559 A * | 8/1969 | Silverman et al. | 433/15 |
| 3,464,113 A * | 9/1969 | Silverman et al. | 433/11 |
| 3,946,488 A * | 3/1976 | Miller et al. | 433/11 |
| 4,184,254 A * | 1/1980 | Kraus | 433/17 |
| 4,192,070 A | 3/1980 | Lemchen et al. | |
| 4,353,692 A | 10/1982 | Karrakussoglu | |
| 4,496,318 A * | 1/1985 | Connelly, Jr. | 433/14 |
| 4,867,678 A | 9/1989 | Parker | |
| 4,897,035 A | 1/1990 | Green | |
| 4,917,602 A | 4/1990 | Broussard | |
| 5,302,121 A | 4/1994 | Gagin | |
| 5,320,525 A | 6/1994 | Forster | |
| 5,356,288 A | 10/1994 | Cohen | |
| 5,931,667 A | 8/1999 | Papandreas | |
| 6,071,118 A | 6/2000 | Damon | |
| 6,168,429 B1 | 1/2001 | Brown | |
| 6,190,166 B1 * | 2/2001 | Sasakura | 433/14 |
| 6,247,923 B1 | 6/2001 | Vashi | |
| 7,033,170 B2 * | 4/2006 | Cordato | 433/10 |
| 7,063,531 B2 | 6/2006 | Maijer et al. | |
| 7,204,690 B2 | 4/2007 | Hanson | |
| 7,267,545 B2 | 9/2007 | Oda | |
| 7,306,457 B2 | 12/2007 | Vigolo | |
| 7,306,458 B1 | 12/2007 | Lu | |
| 7,367,800 B2 | 5/2008 | Lai et al. | |
| 7,396,230 B2 | 7/2008 | Abels et al. | |
| 7,396,457 B2 | 7/2008 | Kwon et al. | |
| 7,431,586 B1 | 10/2008 | Silverman | |
| 7,481,651 B2 | 1/2009 | Sernetz et al. | |
| 7,597,553 B2 | 10/2009 | Kimura | |
| 7,704,072 B2 | 4/2010 | Damon | |
| 7,722,354 B1 | 5/2010 | Dumas | |
| 7,731,496 B2 | 6/2010 | Minium | |
| 7,740,475 B2 | 6/2010 | Minium | |
| 7,771,640 B2 | 8/2010 | Cosse | |
| 7,785,102 B2 | 8/2010 | Papadopoulos | |
| 7,819,660 B2 | 10/2010 | Cosse | |
| 7,828,549 B1 | 11/2010 | Wildman | |
| 7,837,466 B2 | 11/2010 | Griffith et al. | |

(Continued)

*Primary Examiner* — Ralph Lewis
(74) *Attorney, Agent, or Firm* — Caesar, Rivise, Bernstein Cohen & Pokotilow, Ltd.

(57) ABSTRACT

An orthodontic bracket assembly adapted for securement to teeth of the upper and lower jaw is provided. The assembly is a multi-component system that includes a base component and a bracket component. The base component is adapted for securement to a tooth using an adhesive material and includes a housing having an integral channel guide. The bracket component includes a flange arranged for insertion within the channel guide and is held therein by a spring clip. The bracket component includes an archwire retention head for receiving and retaining an orthodontic archwire therein. In one embodiment, the archwire retention head includes a tube having an archwire tunnel extending mesial-distally therethrough. The cross-sectional shape of the archwire tunnel can vary depending upon the archwire being employed and may provide a frictional or frictionless fit. The tube may be positioned at a predetermined location for correcting a maloccluded tooth.

24 Claims, 8 Drawing Sheets

(56) References Cited

U.S. PATENT DOCUMENTS

| | | |
|---|---|---|
| 7,909,603 B2 | 3/2011 | Oda |
| 8,002,543 B2 | 8/2011 | Kang et al. |
| 8,057,226 B2 | 11/2011 | Wiechmann et al. |
| 8,070,488 B2 | 12/2011 | Cosse |
| 8,152,519 B1 | 4/2012 | Dumas |
| 8,157,562 B2 | 4/2012 | Swain |
| 8,162,660 B2 | 4/2012 | Rudman |
| 2004/0131989 A1 | 7/2004 | Dellinger |
| 2005/0186525 A1 | 8/2005 | Abels et al. |
| 2006/0269891 A1 | 11/2006 | Miqui |
| 2007/0082315 A1 | 4/2007 | Sabater |
| 2007/0128571 A1 | 6/2007 | Kimura |
| 2009/0291404 A1 | 11/2009 | Oda |
| 2009/0298003 A1 | 12/2009 | Wei et al. |
| 2010/0021857 A1 | 1/2010 | Kooiman |
| 2010/0092903 A1 | 4/2010 | Sabilla |
| 2010/0196838 A1 | 8/2010 | Damon |
| 2011/0020762 A1 | 1/2011 | Kanomi et al. |
| 2011/0033811 A1 | 2/2011 | Swain |
| 2011/0033812 A1 | 2/2011 | Swain |
| 2011/0039225 A1 | 2/2011 | Hagelganz et al. |
| 2011/0059414 A1 | 3/2011 | Hirsch |
| 2011/0151391 A1 | 6/2011 | Shih et al. |
| 2011/0183280 A1 | 7/2011 | Cosse et al. |
| 2011/0189623 A1 | 8/2011 | Moon et al. |
| 2011/0195372 A1 | 8/2011 | Oda |
| 2011/0311933 A1 | 12/2011 | Parker |
| 2011/0311934 A1 | 12/2011 | Kantomaa |
| 2011/0311935 A1 | 12/2011 | Dumas |
| 2012/0028207 A1 | 2/2012 | Cleary et al. |

* cited by examiner

MULTI-COMPONENT ORTHODONTIC BRACKET ASSEMBLY

CROSS-REFERENCE TO RELATED APPLICATIONS

"Not Applicable"

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

BACKGROUND OF THE INVENTION

Orthodontic brackets, often referred to as "braces", are dental devices used to guide tooth movement during orthodontic treatment. Brackets are manufactured with specific "prescriptions" which are designed to produce ideal positions of the teeth based on average anatomical size and shape of the teeth. Brackets are typically manufactured in specific dimensions, with the most common sizes of brackets having working surfaces (slots) in 0.018×0.025 inch and 0.022×0.025 inch dimensions. Either of these measurements allows for an arch wire of similar dimension to be placed in the slot and used to assist in the movement of teeth.

These brackets are typically made of either stainless steel, titanium, plastic composites, or ceramic material and are normally affixed to the teeth of an individual, by the use of cement or another type of bonding agent, and are adapted to receive a wire which is formed and deployed in the brackets (e.g., in the mouth of a patient) in order to provide therapeutic force or pressure on the patient's teeth. The combination of the brackets and the wire are often sometimes collectively referred to as a "bracket system" or an "orthodontic appliance system".

While such prior and currently utilized bracket systems do allow therapeutic pressure to be applied to a patient's teeth, they suffer from some drawbacks. By way of example and without limitation, as the therapy is applied to the patient (i.e., over time) positional modifications may need to be made to the brackets or different brackets may be optimally needed. This "bracket repositioning" or "replacement" is complicated and time consuming because the currently utilized brackets must be forcibly removed from the patient's teeth (e.g., removed from the cement or adhering agent), the teeth must be cleaned and "re-prepped" (an etching agent and a new application of an adhering agent must be deployed on the teeth), and the new or modified brackets must be replaced on the newly prepped teeth. The process is uncomfortable to the patient and is relatively costly due to the need for additional etching and adhesive material and the time needed to achieve the change or modification. Moreover, sometimes the deployed brackets become broken or are in need of repair and must be removed from the patient's teeth to become serviced, thereby requiring the same sort of previously described process and relatively the same sort of cost and discomfort.

Further, different sorts of brackets or attachments may be used on a patient, within a certain time, to better allow or control certain tooth movements, or to adjust for variable tooth anatomy and the phase of treatment such as alignment, leveling, space closure or finishing (i.e., each patient may experience different amounts and types of therapy with a certain bracket).

In addition, traditional bracket systems generally rely on active ligation using elastomeric or wire ligatures wrapped about the tie wings of the bracket to hold the archwire onto the archwire slot. This binding creates friction during orthodontic tooth movement and consequently increases the forces needed for leveling and sliding tooth movement during treatment. By contrast, passive self-ligating (or so-called frictionless) bracket systems, or bracket systems that do not require traditional ligatures or ligating modules, have been developed which rely on a principle that forces employed to reposition teeth should not overwhelm the supporting periodontium and facial musculature. Forces applied should instead be minimized to a level just large enough to stimulate cellular activity and, thus, tooth movement without unnecessarily disturbing the vascular supply to the periodontium.

Several self-ligating (ligatureless) orthodontic brackets have been designed. Some are passive and some are active. However, most of those have complex designs, incorporating features requiring prohibitively expensive machining operations or comprising multiple separate parts, which in turn increases the number of failure modes for such brackets. Other designs have been rejected in the marketplace due to poor quality or poor design, a lack of available features, difficulty of use, or other factors.

There is therefore a need for a new and improved orthodontic bracket assembly which allows brackets and orthodontic bracket systems to be easily, quickly, and cost effectively deployed upon the teeth of a patient and it is one non-limiting object of the present invention to provide such an improved orthodontic bracket system. Such an orthodontic bracket system should also incorporate a passive self-ligating capability to reduce unwanted friction.

SUMMARY OF THE INVENTION

In accordance with the present invention, an orthodontic bracket assembly adapted for securement to teeth of the upper and lower jaw is provided. The assembly is a multi-component system that includes a base component and a bracket component. The base component is designed to be bonded to a tooth and includes a peripheral housing having an integral channel guide. The bracket component includes a flange arranged for insertion within the channel guide and is held therein by a spring clip. The bracket component includes an archwire retention head for receiving and retaining an orthodontic archwire therein. In one embodiment, the archwire retention head includes a tube having an archwire tunnel extending mesial-distally therethrough. The cross-sectional shape of the archwire tunnel can vary depending upon the archwire being employed and may provide a frictional or frictionless fit. The tube may be positioned at a predetermined location for correcting a maloccluded tooth. The base component and/or the bracket component can be made of any suitable material currently in use including but not limited to stainless steel, metallic alloys (deformable or rigid), plastic alloys, or ceramic alloys.

DETAILED DESCRIPTION OF THE PREFERRED EMBODIMENT

Figure 1:
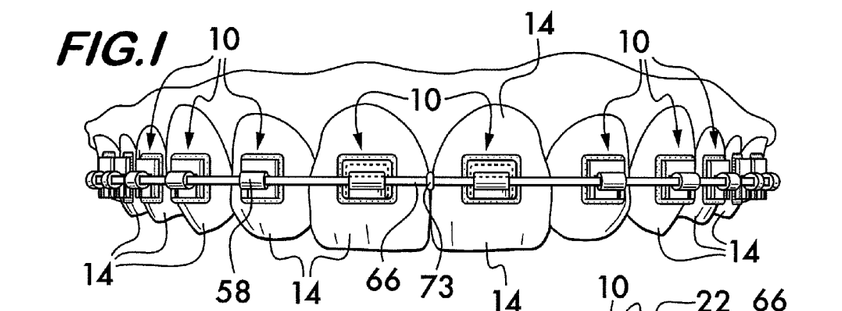
FIG. 1 is a perspective view of a first embodiment of the orthodontic bracket assembly of the present invention affixed to teeth located in the upper jaw of a patient.
Figures 2, 2A:
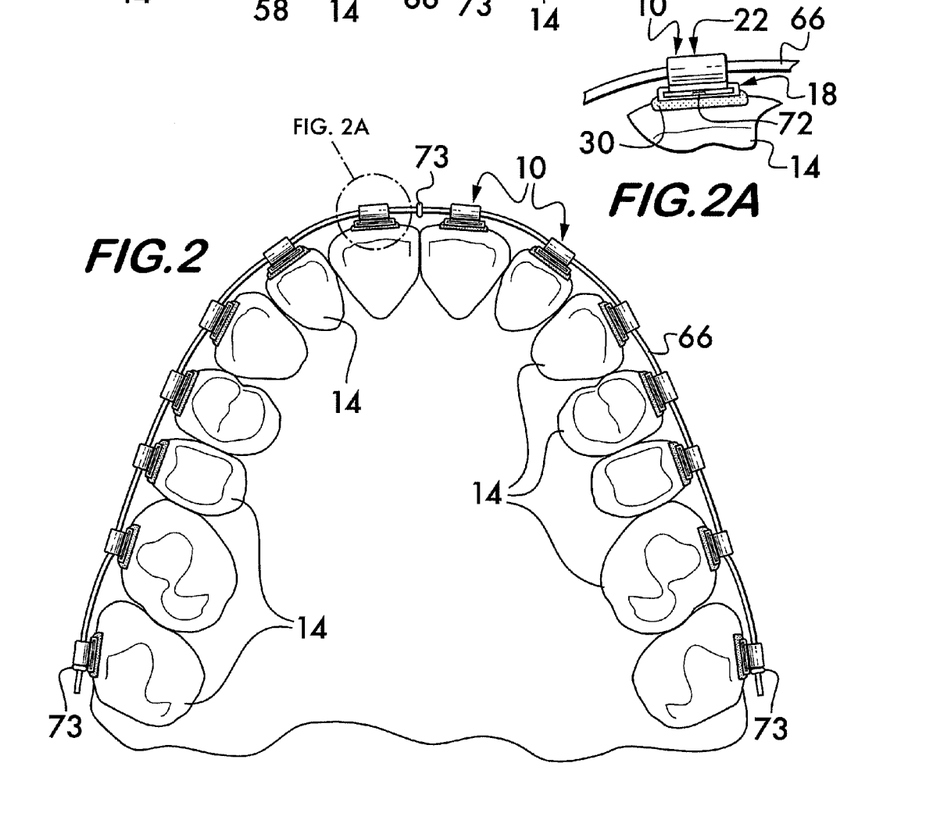
FIG. 2 is another perspective view of the first embodiment of the orthodontic bracket assembly of the present invention affixed to teeth located in the upper jaw of a patient.
FIG. 2A is an enlarged perspective view of an encircled portion of FIG. 2.
Figure 3:
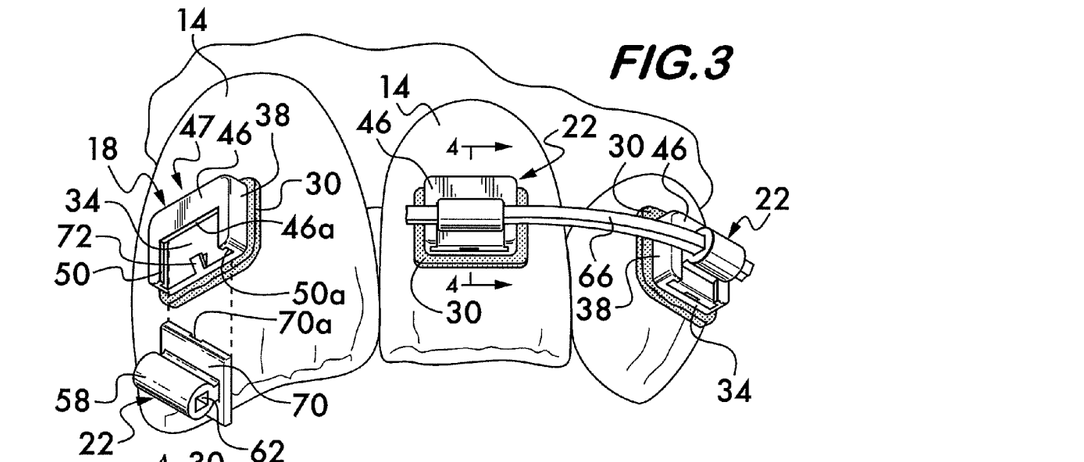
FIG. 3 is an enlarged perspective view of the first embodiment of the orthodontic bracket assembly of the present invention illustrating the manner for inserting the tube assembly into a base component in a vertical direction.

Referring now in detail to the various figures of the drawings wherein like reference characters refer to like parts, there is shown at 10 in FIGS. 1-3, a first embodiment of the present invention. The first embodiment includes a plurality of orthodontic brackets 10 bonded to the front surface of a plurality of adjacent teeth 14 of the maxilla, or upper jaw, of a patient, the teeth 14 requiring corrective orthodontic alignment. It should be understood that alternatively, the orthodontic brackets 10 of the present invention could be applied to adjacent teeth of the lower jaw, or of both the upper and lower jaws. Referring now to FIG. 3, each of the orthodontic brackets 10 is a multi-component system including a base component 18 adapted to be secured to the tooth and a bracket component 22 arranged to be retained within the base component 18.

Figure 4:
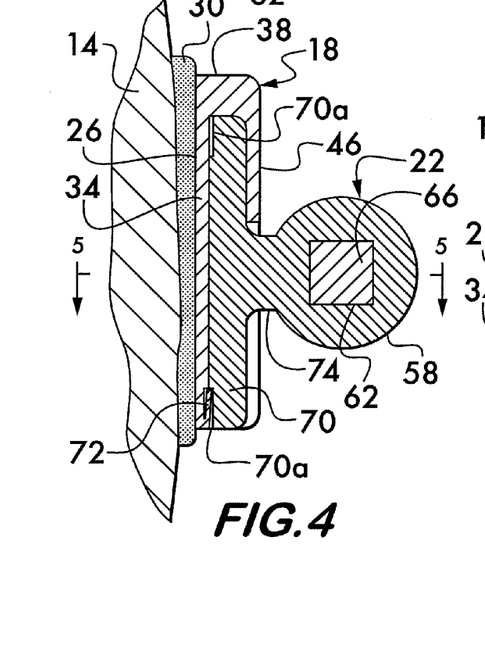
FIG. 4 is a sectional view through lines 4-4 of FIG. 3.
Figures 5, 5A:
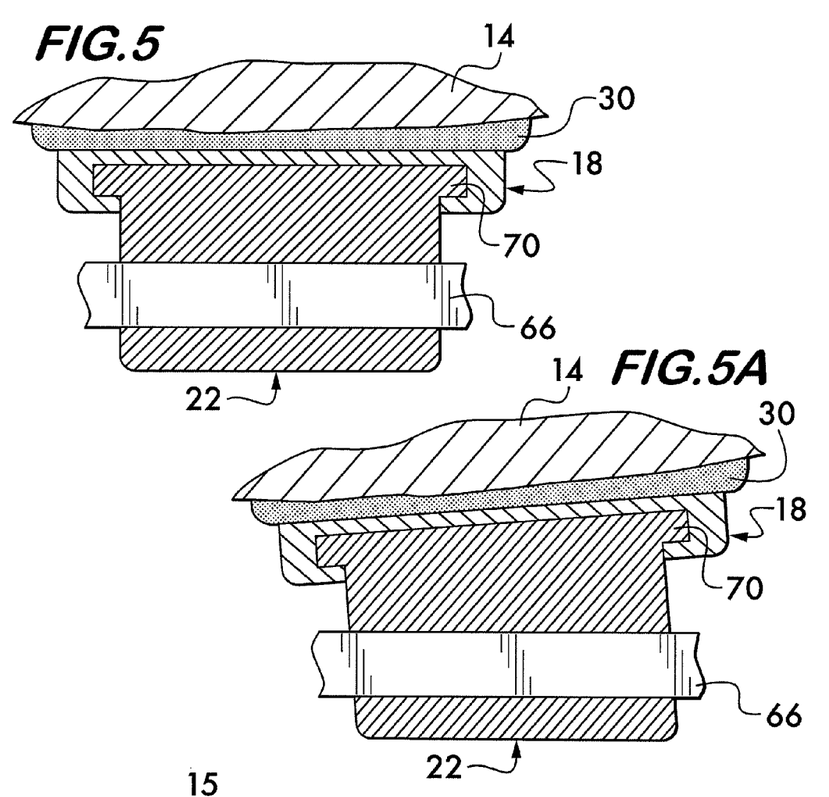
FIG. 5 is a sectional view through lines 5-5 of FIG. 4.
FIG. 5A is an enlarged view of the first embodiment of the orthodontic bracket assembly of the present invention arranged for rotational movement of a tooth.

Referring now to FIGS. 3-5, each base component 18 includes a back surface 26 which is arranged for attachment to a tooth 14 utilizing a suitable adhesive 30 or other bonding material. For example, the back surface 26 may be provided with or include a mounting pad made of stainless steel or other alloys, including metal, plastic or ceramic, as are currently in use, to enable the base component 18 to be bonded to the tooth 14 with the suitable adhesive 30. The back surface 26 may include a customary slight concave configuration to match the natural convexity of the outer surface of the tooth 14 and have an irregular underside of mesh or undercut dimple design to enhance the bonding of the pad as is customary in orthodontics. As best illustrated in these figures, the bonding material 30 extends beyond the back surface 26 of the base component 18.

Each base component 18 includes a floor 34 that is generally rectangular in shape. The base component 18 also includes a continuous sidewall 38 that may be integral with the floor 34. The sidewall 38 extends substantially around the perimeter of the floor 34 on three sides and merges into a top wall 46 that includes an open portion indicated at 46A. Together, the floor 34, sidewall 38 and top wall 46 form a housing 47 that includes an integral channel guide 50 having a front entranceway 50a. The integral channel guide 50 is provided to accept entry of and retention of a bracket component 22 within the base component 18, as described in detail below. Alternatively, the entranceway of the channel guide 50 may be flared to facilitate entry into the base component 18.

In this first embodiment, the bracket component includes an archwire retention head in the form of a tube 58 having an archwire tunnel 62 extending mesial-distally therethrough. The archwire tunnel 62 is arranged for receiving an orthodontic archwire 66 therethrough. The cross-sectional sizes of the archwire tunnel 62 and orthodontic archwire 66 may be selected in a manner to obtain a low-friction relationship or even a zero-friction relationship, as may be required to overcome the drawbacks relating to friction previously discussed.

Figure 4A:
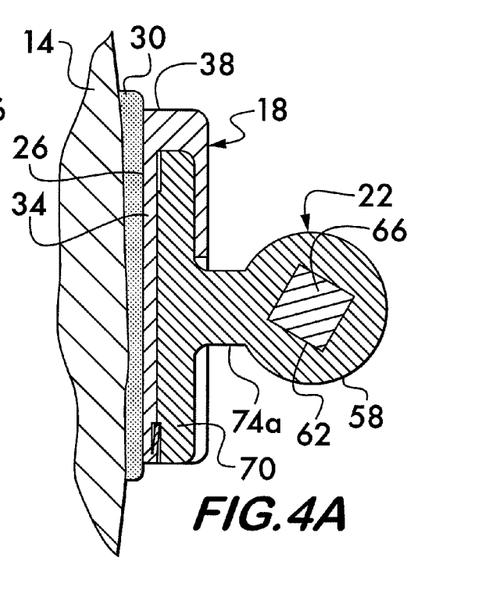
FIG. 4A is sectional view of the orthodontic bracket assembly of the present invention including a more traditional rectangular or square-shaped arch tunnel that is oriented to enable an archwire to apply a torque to the root of a tooth.

Referring now to FIGS. 4 and 4A, the archwire tunnel 62 may include a cross-sectional shape that is either a more traditional rectangular shape or a square shape for the purpose of accommodating the typical sized orthodontic archwires 66. Alternatively, the cross-sectional shape of the archwire tunnel 62 may be oval, round, triangular, hexagonal, octagonal, trapezoidal, polygonal, a parallelogram, or a free-form combination of lines and arcs for the purpose of accommodating similar sized orthodontic archwires, i.e., 0.016" round, 0.016"×0.016" square, and 0.017"×0.025" rectangular cross-sections. As best shown in FIG. 4A, a square-shaped archwire tunnel 62 is provided that is oriented at a diagonal orientation to enable a square-shaped archwire 66 extending therethrough to apply a torque to the root of a tooth 14 to move the tooth to a desired position.

Referring now to FIGS. 3 through 5A, the tube 58 of the bracket component 22 is mounted to or is integral with a flange 70. The flange 70 includes a flat planar surface and is elongated in the mesial-distal direction, e.g., generally rectangular in shape. The flange 70 includes rounded corners to avoid sharp edges. The flange 70 is arranged for sliding into the channel guide 50 through entranceway 50a for retaining the bracket component 22 within the base component 18. To provide such retention, the bottom surface of the flange 70 is provided with a pair of centrally-located retention openings 70a located on opposite edges of the flange 70. The floor 34 of the base component 18 is provided with a centrally-located resilient spring tab 72 that may be integral with the base component 18 and aligned with the retention openings 70a of the flange 70. The spring tab 72 is normally biased to extend away from the floor 34 and upwardly into the housing 47. As the flange 70 of the bracket component 22 is slid into the channel guide 50 of the base component 18, the spring tab 72 is caused to be deflected out of its normal position. As the flange 70 reaches its terminal position within the channel guide 50, a retention opening 70a moves over the spring tab 72, thus causing the spring tab 72 to move from its deflected position to its normal position within the retention opening 70a, to lock the bracket component 22 into the base component 18 as best shown in FIG. 4. When it is desired to remove the bracket component 22 from the base component 18, insertion of a suitable orthodontic instrument within the retention opening 70a will return the spring tab 72 to its deflected position to enable easy release and removal of the bracket component 22 from the base component 18. By providing retention openings 70a on opposite sides of the flange 70, the bracket component 22 may slide into and be retained within the base component 18 regardless of the orientation of the flange 70.

In this manner, as therapy is applied to a patient over a period of time and teeth progress towards their corrected positions, the bracket components 22 may easily be removed from their corresponding base components 18 without the need to forcibly remove the base component 18 from the teeth 14. Thus, new progressively biased bracket components 22 may be deployed onto the base components 18 having different features for applying different therapeutic pressures to a patient's teeth 14. The new bracket components 22 may be deployed relatively quickly, and with less expense and discomfort.

As best shown in FIGS. 1 and 2, again utilizing a suitable orthodontic instrument, an entire set or group of bracket components 22, e.g., up to a total of fourteen or more bracket components 22, may readily be removed in sequence from their corresponding base components 18. Once removed from the base components 18, the bracket components 22, remaining threaded onto the archwire 66, may be removed from a patient's mouth as a group. The bracket components 22 may then be removed from the archwire 66 and replaced with new bracket components 22 provided according to specific prescriptions for insertion into the base components 18 to achieve desired movement of teeth 14. In this manner, as therapy is applied to the patient over a period of time and teeth 14 progress towards their corrected positions, the bracket components 22 may be removed from the base component 18 and sequential and progressively biased bracket components 22 may be inserted into the base component 18 and utilized to move teeth from their initial maloccluded positions to a near finished and corrected state. In this manner, the base component 18 does not need to be forcibly removed from the patient's teeth (e.g., removed from the cement or adhering agent). The need for teeth to be cleaned and re-prepped is eliminated. Moreover, if a bracket component 22 becomes broken or is in need of repair, the base component 18 does not need to be forcibly removed from the teeth to replace or repair the bracket component 22.

Figure 6:
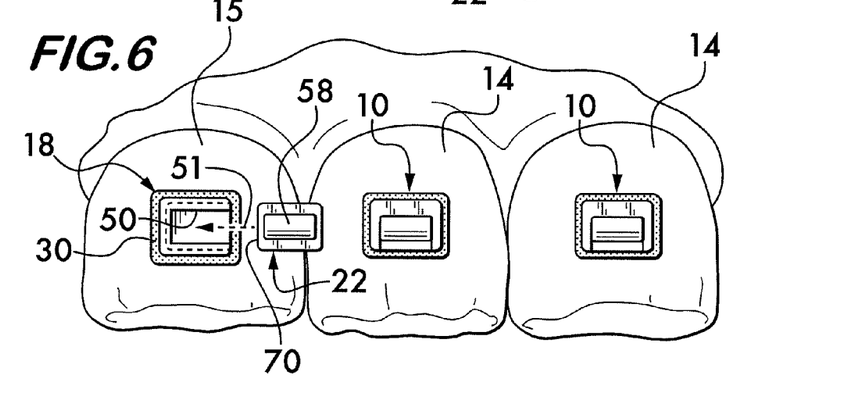
FIG. 6 is another enlarged perspective view of the first embodiment of the orthodontic bracket assembly of the present invention fixedly mounted to several teeth illustrating the manner for inserting the tube assembly of the bracket assembly into a base component in a mesial-distal direction.

As shown in FIGS. 3 and 4, the base component 18 of each orthodontic bracket 10 is oriented on a corresponding tooth 14 located in the upper jaw such that insertion of the flange 70 of the bracket component 22 may be in an upward direction from the occlusal surface to the gingival surface of the tooth 14. Similarly, where the base components 18 are located on teeth 14 of the lower jaw (not shown), insertion of the flange 70 of the bracket component 22 may be in a downward direction from the occlusal surface to the gingival surface of the tooth of the lower jaw. However, it should be understood that the base component 18 may be oriented on the teeth 14 in any number of directions to accept insertion of a corresponding bracket component 22. For example, referring now to FIG. 6, there is shown a base component 18 attached to a molar 15 located in the back of the mouth behind several premolar teeth 14 where insertion of the bracket component 22 in a vertical direction may be difficult. The channel guides 50 of the base component 18 are oriented in a horizontal direction facing mesially as opposed to being oriented vertically, as shown in the pre-molar teeth. In this manner, the channel guides 50 of the base component 18 are oriented horizontally to accept insertion of the bracket component 22 in a mesial-distal direction, as indicated by arrow 51.

Referring now to FIG. 2, a plurality of retaining members 73 may be slipped onto the archwire 66 at opposite ends thereof to prevent the bracket components 22 from sliding off the ends of the archwire 66 during their insertion into or removal from the base components 18, already mounted to the teeth 14. One or more additional retaining members 73 may be positioned between the bracket components 22, such as at the midline, to separate the bracket components 22 positioned to the left of the midline from the bracket components 22 positioned on the right side of the midline. The retaining members 73 may be in the form of an O-ring formed of a suitable elastic material, e.g., rubber stoppers, that will frictionally engage with the archwire 66.

Referring now to FIGS. 4, 4A, 8 and 9, the bracket component 22 may include a neck 74 that is sized to provide a predetermined offset distance between the flange 70 and the archwire tunnel 62 in accordance with a specific "prescription" to effect in-out movement of teeth in a buccal-lingual direction to new positions to correct malloclusions. For example, a bracket component 22 may be provided wherein a neck 74 is incorporated that is comparatively larger or comparatively smaller in size to effect in-out movement (translation) of teeth. In FIGS. 4 and 4A, it can be seen that the neck 74A of the bracket component 22 is relatively larger in size than the neck 74 of bracket component 22 of FIG. 4. As a result, the distance between the archwire tunnel 62 and the outer surface of tooth 14 in FIG. 4A is larger than the distance between the archwire tunnel 62 and the tooth surface 14 in FIG. 4.

Figure 8:
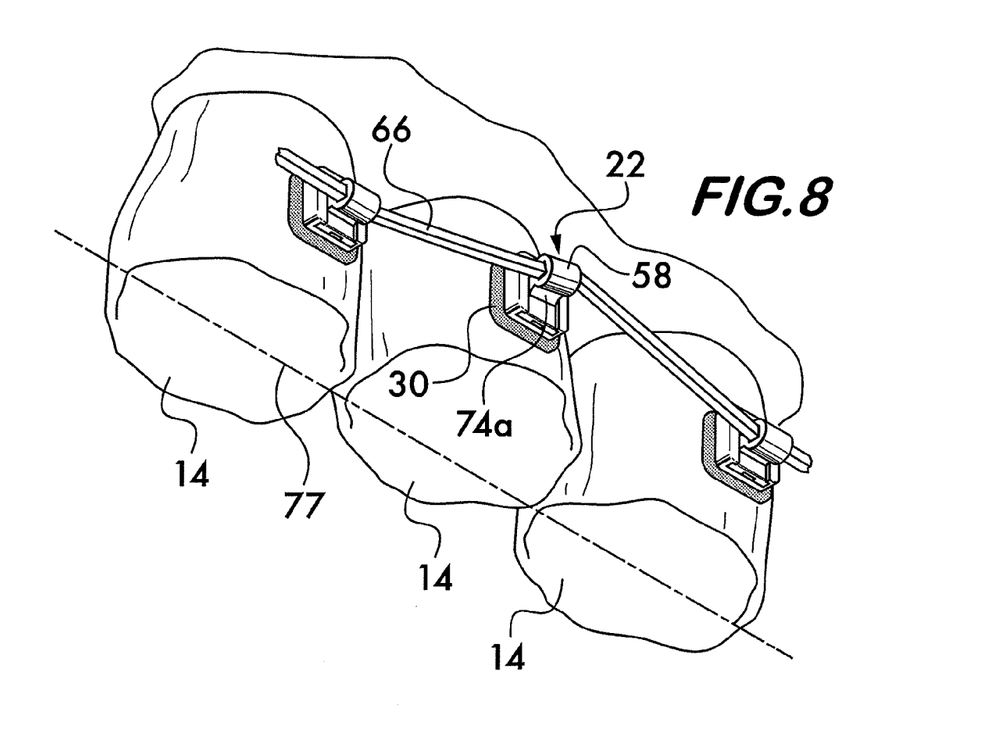
FIG. 8 is an enlarged perspective view of the first embodiment of the orthodontic bracket assembly of the present invention fixedly mounted to several teeth illustrating its use for applying an angular, rotational, and translational force to a tooth.

Referring now to FIG. 8, there is shown three teeth 14 positioned along a centerline 77, the two outer teeth 14 being centered over the centerline 77, and the middle tooth 14 being misaligned with respect to the centerline 77. When it is desired to translate a tooth 14 in the lingual direction, i.e., towards the tongue, to align said tooth 14 with adjacent teeth 14, a relatively larger neck 74A (also shown in FIG. 4A) may be incorporated into the bracket component 22 to cause the archwire 66 to apply a translational force on the tooth 14 to move the tooth in a lingual direction to a desired position. It should be noted that, additionally, the tube 58 shown in FIG. 8 is set at a predetermined angle to correct an undesirable rotation of tooth 14, as a prescription may require an orthodontic bracket to move a tooth to address multiple malocclusions, e.g., angular, rotational, and translational movement.

Figure 9:
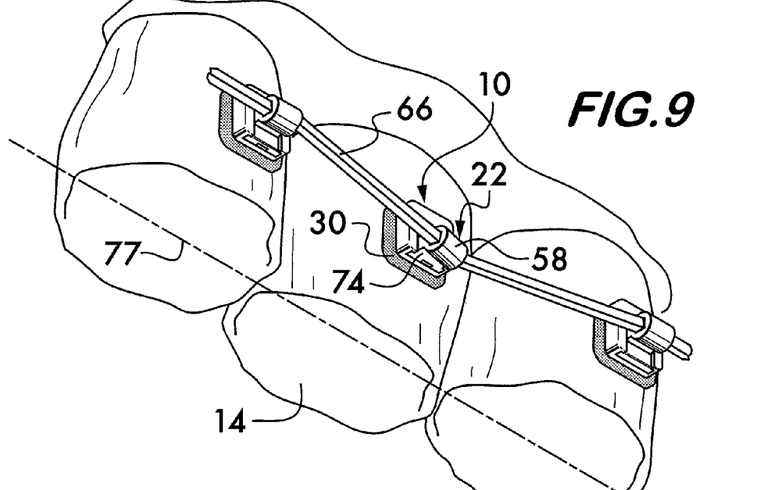
FIG. 9 is an enlarged perspective view of the first embodiment of the orthodontic bracket assembly of the present invention fixedly mounted to several teeth illustrating its use for applying an angular, rotational, and translational force to a tooth.

Referring now to FIG. 9, conversely, when it is desired to translate a tooth 14 in a buccal direction to align it with adjacent teeth along a centerline 77, a bracket component 22 may be employed on an orthodontic appliance 10 that incorporates a relatively smaller neck 74 (also shown in FIG. 4) or no neck whatsoever to cause the archwire 66 to apply a translational force on the tooth 14 to move the tooth 14 in a buccal direction to bring the tooth into alignment with adjacent teeth. It should be noted that, additionally, the tube 58 shown in FIG. 9 is set at a predetermined angle to also correct undesirable angulation and rotation of tooth 14.

Figures 10, 11:
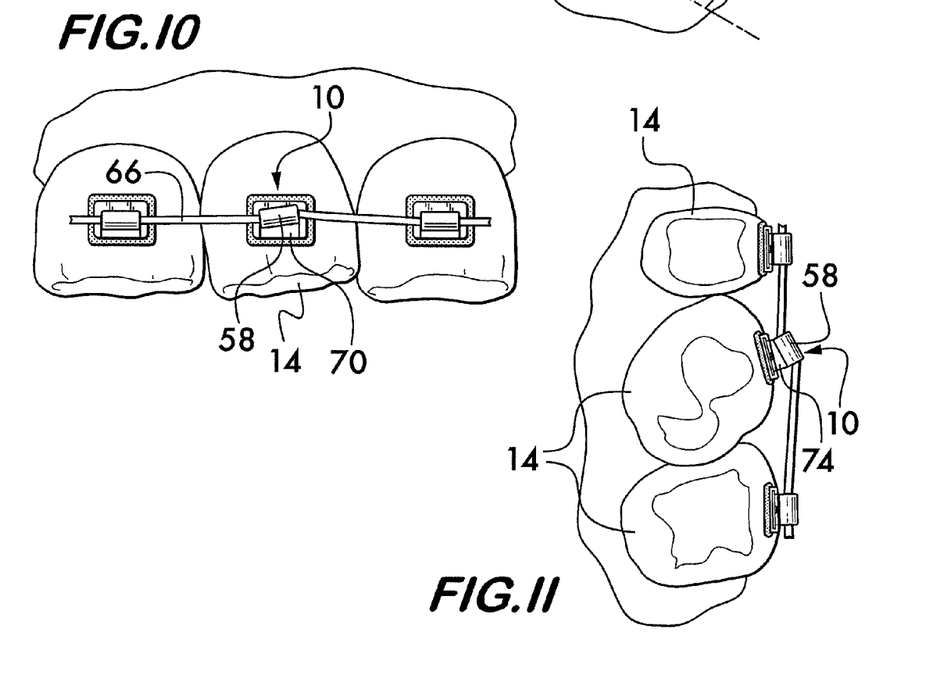
FIG. 10 is an enlarged perspective view of the first embodiment of the orthodontic bracket assembly of the present invention fixedly mounted to several teeth illustrating its use for correcting the position of a tooth that is significantly angulated.
FIG. 11 is an enlarged perspective view of the first embodiment of the orthodontic bracket assembly of the present invention fixedly mounted to several teeth illustrating its use for correcting the position of a tooth that is significantly rotated.

Referring now to FIG. 10, in accordance with yet another aspect of the present invention, there is shown a perspective view the orthodontic appliance 10 secured to a tooth 14, the tooth having an undesirable angulated orientation. Under this aspect of the invention, a bracket component 22 is provided with a tube 58 that is manufactured in accordance with a specific prescription to address the angulated orientation of the tooth 14. The tube 58 is situated on the flange 70 at a desired fixed inclination or angle from its mesial end to its distal end for correction of the angulated tooth 14. As is illustrated in FIG. 10, the base component 18 attached to the tooth 14 having the undesirable angulation is aligned with the base components 18 on adjacent teeth 14. The archwire 66 extending through the angled archwire tunnel 62 of the tube 58, will cause movement of the tooth 14 to correct the angulated orientation and move the tooth 14 to a desired corrected position.

Referring now to FIG. 11, in accordance with yet another aspect of the present invention, there is shown a perspective view of the orthodontic bracket assembly 10 secured to an undesirably rotated tooth 14. To accomplish the goal of correcting such a rotated tooth, the base component 18 and bracket component 22 of the orthodontic bracket assembly 10 of the present invention are provided in a size that is smaller than a conventional prior art orthodontic bracket. Thus, the orthodontic bracket assembly 10 may be suited for fitting within the confines of a small space between a rotated tooth 14 and an adjacent tooth 14. Alternatively, the overall size of the base component 18 and the bracket component 22 may be reduced as needed to fit within the confines of such small spaces. The orthodontic bracket assembly 10, or a version thereof that is reduced in size, may then be affixed to the rotated tooth 14 at a suitable place for rotation.

Also, as shown in FIG. 11, the neck 74 is configured to retain the tube 58 at a predetermined angle with respect to the archwire 66. In this manner, the archwire 66 extending through the archwire tunnel of the tube 58 will cause movement of the rotated tooth 16 in a clockwise direction to a corrected position. Once the tooth has been moved to the corrected position, the bracket component 22 may readily be removed from the base component 18 and replaced with a larger and more standard sized bracket component 22 for further corrective movement.

Figure 12:
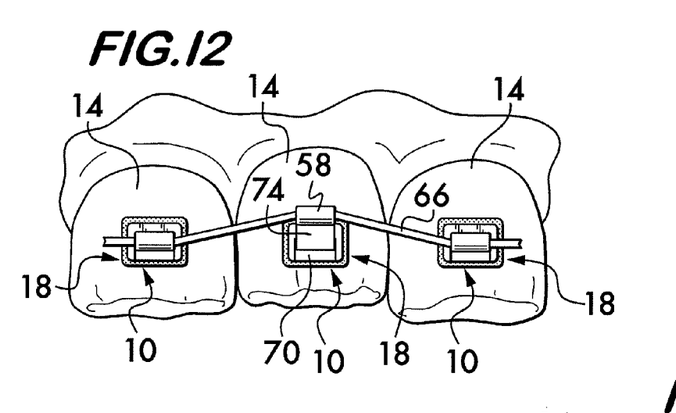
FIG. 12 is an enlarged perspective view of the first embodiment of the orthodontic bracket assembly of the present invention fixedly mounted to several teeth illustrating its use for correcting the vertical position of a tooth.

Referring now to FIG. 12, in accordance with yet another aspect of the present invention, there is shown a perspective view of the orthodontic bracket assembly 10 of the present invention secured to an undesirably positioned tooth 14, i.e., a tooth that is situated higher than adjacent teeth. As is illustrated in the figure, the base component 18 attached to the undesirably high tooth 14 is aligned with the base components 18 on adjacent teeth 14. However, the bracket component 22 includes a neck 74 that is relatively larger and extends at an angle towards the gingival surface of the tooth to position the tube 58 above the tubes 58 on adjacent teeth 14. In this manner, the archwire 66 extending through the archwire tunnel 62 of the tubes 58 will cause movement of the undesirably positioned tooth 14 downwardly to a corrected position.

Figure 13:
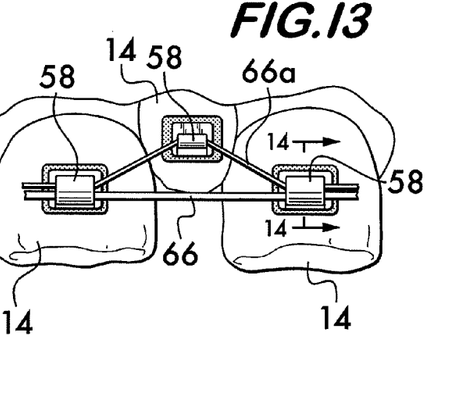
FIG. 13 is an enlarged perspective view of a second embodiment of the orthodontic bracket assembly of the present invention fixedly mounted to several teeth wherein the tube includes an auxiliary archwire tunnel for passage of a second archwire therethrough for moving a significantly misaligned tooth, such as one that has erupted in the palate.
Figure 14:
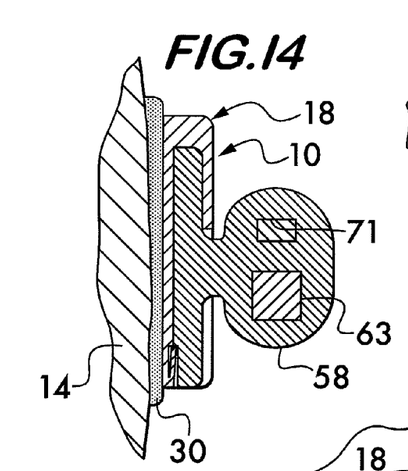
FIG. 14 is a sectional view through lines 14-14 of FIG. 13.

Referring now to FIGS. 13 and 14, in accordance with yet another aspect of the present invention, there is shown a bracket component 22 including two differently shaped archwire tunnels, i.e., a larger square-shaped main archwire tunnel 63 and a smaller rectangular-shaped auxiliary archwire tunnel 71. The archwire tunnels 63, 71 may include different cross-sectional shapes and sizes, e.g., square, substantially round, rectangular, oval, triangular, hexagonal, octagonal, trapezoidal, polygonal, parallelogram, for the purpose of accommodating similarly sized or differently sized orthodontic archwires 66. As best shown in FIG. 13, in the event a tooth 14 is substantially misaligned, e.g., erupted in the palate, a substantially lighter flexible archwire 66a may be utilized to align that tooth 14 with other aligned teeth 14. The aligned teeth 14 may remain attached to the main archwire 66 passing through archwire tunnel 63 while the flexible archwire 66a, passing through archwire tunnel 71, is utilized to bring the misaligned tooth 14 into alignment, thus preventing distortion of the aligned teeth. Alternatively, in accordance with the present invention, a plurality of tubes 58 may be integral with or mounted to a single flange 70. The plurality of archwire tunnels 63, 71 may include different cross-sectional shapes and sizes, e.g., square, substantially round, rectangular, oval, triangular, hexagonal, octagonal, trapezoidal, polygonal, parallelogram, for the purpose of accommodating similarly sized or differently sized orthodontic archwires. Alternatively, the archwire tunnels 63, 71 may be of the same cross-sectional shape.

Figure 15:
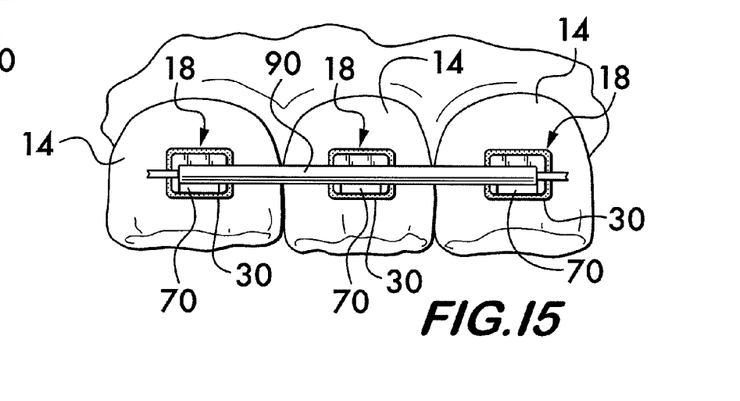
FIG. 15 is an enlarged perspective view of a third embodiment of the orthodontic bracket assembly of the present invention fixedly mounted to three adjacent teeth.

Referring now to FIG. 15, often it is desirable to move a group of aligned teeth together as a single unit. In accordance with yet another aspect of the present invention, there is shown a single tubular bar 90 extending across a plurality of teeth 14, e.g., three teeth. The tubular bar 90 is provided for coupling and retaining together a plurality, e.g., two or more, teeth for movement as a group. In the manner discussed above, a base component 18 is attached to each tooth 14 utilizing a suitable adhesive or other bonding material 30. The single elongated tubular bar 90 extends across the length of the plurality of teeth 14. Mounted to the tubular bar 90 is a plurality of flanges 70 located at positions corresponding to each of the base components 18. In this manner, the flanges 70 may be inserted into and retained within the base components 18 in the manner previously described to retain the plurality of teeth 14 together and move them as a single unit.

Figure 7:
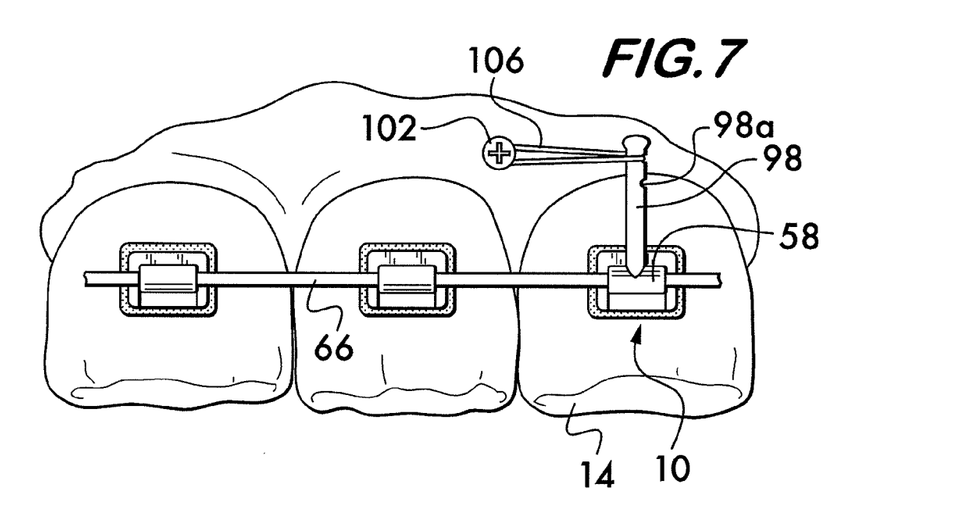
FIG. 7 is an enlarged perspective view of the first embodiment of the orthodontic bracket assembly of the present invention fixedly mounted to several teeth illustrating its use in combination with a power arm.

Referring now to FIG. 7, in accordance with yet another aspect of the present invention, it should be mentioned that a power arm 98 can be used in combination with the orthodontic bracket assembly 10. The power arm 98 may be integral with the tube 58 and extends vertically therefrom for connection to an anchor screw 102 located in the bone. The power arm 98 is provided with a plurality of grooves 98a for connection to the anchor screw 102 utilizing a suitable elastic band 106 or other means, such as a spring (not shown). Other devices, such as crimpable hooks arranged to be crimped to the archwire 66 between orthodontic bracket assemblies 10 and to which rubber bands or elastics may be attached, may be utilized in combination with the present invention in ways similar to use of such devices in combination with prior art orthodontic bracket assemblies. It should be appreciated from the teachings of the present invention that other conventional orthodontic attachments may be used in combination with the orthodontic bracket assembly 10 of the present invention.

Figure 16:
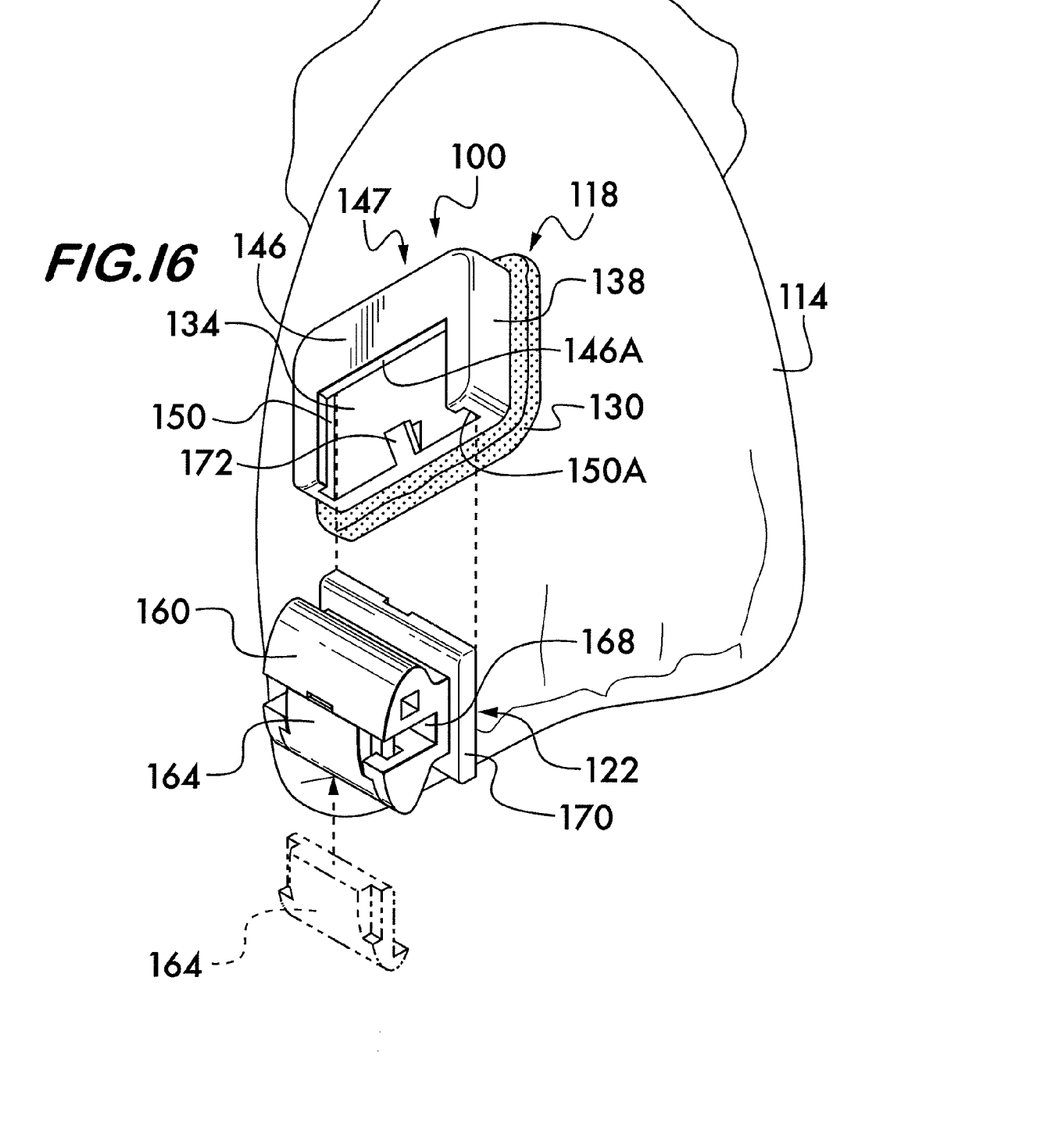
FIG. 16 is an enlarged perspective view of a fourth embodiment of the orthodontic bracket assembly of the present invention fixedly mounted to a tooth; and, FIG. 17 is an enlarged perspective view of a fifth embodiment of the orthodontic bracket assembly of the present invention fixedly mounted to a tooth.

Referring now to FIG. 16, in accordance with yet another aspect of the present invention, there is shown a fourth embodiment 100 of the present invention. As in previous embodiments, this embodiment 100 is a multi-component system including a base component 118 adapted to be secured to a tooth 114 and a bracket component 122 arranged to be retained within the base component 118. As in previous embodiments, the base component 118 is arranged for attachment to the tooth 114 utilizing a suitable adhesive 130 and may be slightly concave to match the natural convexity of the outer surface of the tooth 114. As in previous embodiments, the base component 118 includes a floor 134 that is generally rectangular in shape and a continuous sidewall 138 that may be integral with the floor 134. The sidewall 138 extends substantially around the perimeter of the floor 134 on three sides and merges into a top wall 146 that includes an open portion indicated at 146A. Together, the floor 134, sidewall 138 and top wall 146 form a housing 147 that includes a channel guide 150 having a front entranceway 150A. The channel guide 150 is provided to accept entry and retention of a bracket component 122. That is, the bracket component 122 is provided with a flange 170 that is arranged for sliding into the channel guide 150 through entranceway 150A for retaining the bracket component 122 within the base component 118. As described in earlier embodiments, the floor 134 of the base component 118 is provided with a centrally-located resilient spring tab 172 that is arranged to lock the bracket component 122 into the base component 118.

Under this embodiment, the archwire retention head is in the form of a self-ligating retention member 160. The self-ligating retention member 160 shown in FIG. 16 is merely exemplary. There are numerous varieties of self-ligating systems sold by manufacturers including Dentsply International, Inc. under the trademark In-Ovation; Ortho Organizers, Inc. under the trademark Carriere LX; and Ormco Corporation under the trademark Damon System. The self-ligating retention member 160 may be integral with the flange 170 and may include a movable ligating slide 164 slidably coupled with the self-ligating retention member 160. The ligating slide 164 is arranged to move from an open or unlatched position (shown in phantom) for positioning of an archwire (not shown) within a recessed groove 168 of the retention member 160, to a closed or latched position in which the arch wire (not shown) is captured or enclosed in the recessed groove 168. The recessed groove 168 is arranged to receive an orthodontic archwire (not shown) in the manner known in the art. In use, the ligating slide 164 in the closed position blocks the entrance to the recessed groove 168 to capture the archwire therein. The ligating slide 164 may be unlocked using a suitable tool to provide an unlatched condition for removal of the arch wire. In other specific embodiments of the invention, the self-ligating retention member may assume different constructions, such as a metallic hinged closure, and is not limited to a sliding ligating mechanism.

Figure 17:
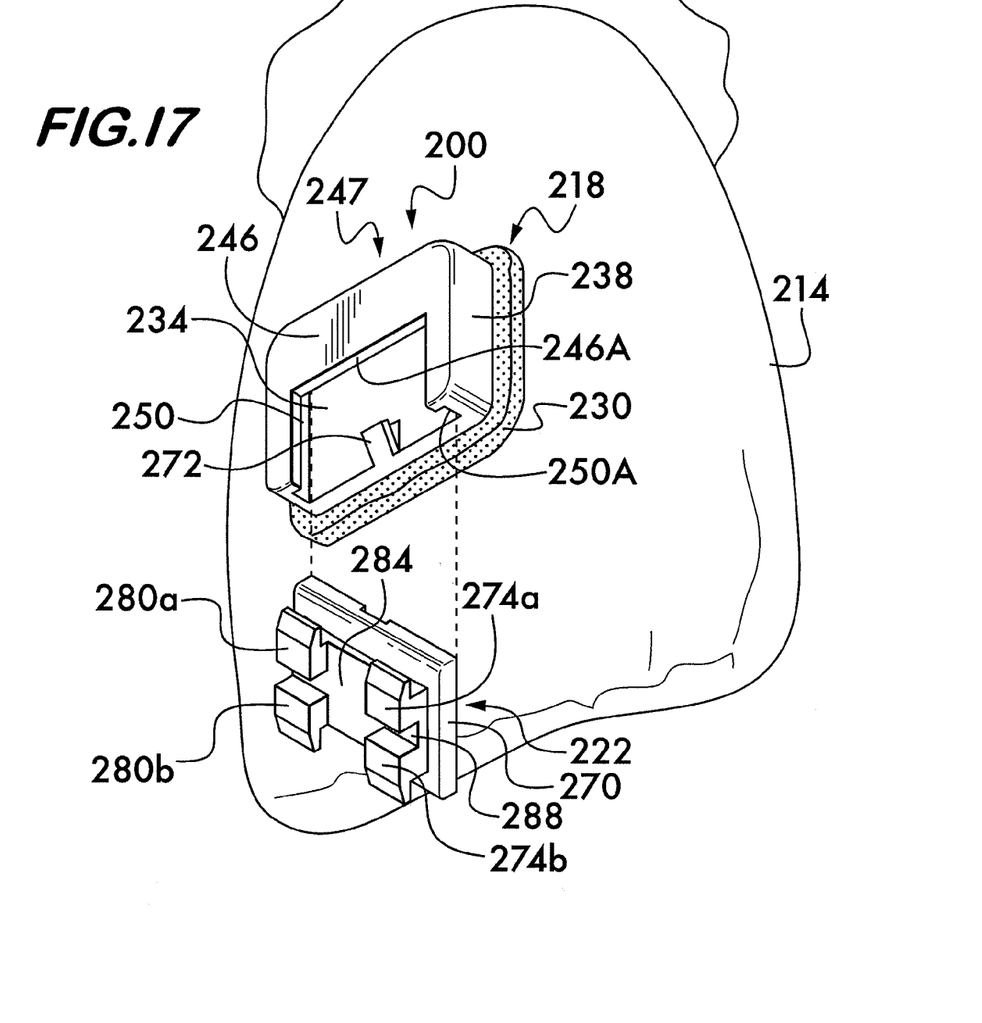

Referring now to FIG. 17, in accordance with yet another aspect of the present invention, there is shown a fifth embodiment 200 of the present invention. As in previous embodiments, this embodiment 200 is a multi-component system including a base component 218 adapted to be secured to a tooth 214 and a bracket component 222 arranged to be retained within the base component 218. As in previous embodiments, the base component 218 is arranged for attachment to the tooth 214 utilizing a suitable adhesive 230. As in previous embodiments, the base component 218 includes a generally rectangular floor 234, a continuous sidewall 238, and a top wall 246 including an open portion 246A, that together form a housing 247 having a channel guide 250 and a front entranceway 250A for accepting entry and retention of the bracket component 222. The bracket component 222 is provided with a flange 270 for retaining the bracket component 222 within the base component 218 in the manner previously described. The floor 234 of the base component 218 is provided with a centrally-located resilient spring tab 272 arranged to retain the bracket component 222 within the base component 218.

The bracket component 222 includes an archwire retention head formed of a mesial pair of spaced-apart tie-wing portions 274a and 274b, and a distal pair of spaced-apart tie-wing portions 280a and 280b, mesial referring to a direction toward the front of the patient's mouth, and distal referring to a direction toward the back of the patient's mouth. The tie-wings are integral with a base portion 284, or alternatively, could be separate elements bonded to the base portion 284. The spaced-apart relationship of the tie-wings defines an archwire slot 288 therebetween which extends horizontally across the bracket component 222. The bracket component 222 shown in FIG. 17 is merely exemplary. There are numerous varieties of tie-wing bracket assemblies sold by manufacturers that could be incorporated for use in accordance with the teachings of the present invention.

While various embodiments have been shown and described, various modifications and substitutions may be made thereto without departing from the spirit and scope of the invention.

I claim:

1. An orthodontic bracket assembly adapted to be secured to a tooth, said assembly comprising:
   a. a base component adapted to be secured directly to a tooth, said base component including a floor and a sidewall extending substantially around the perimeter of said floor on three sides thereof, said sidewall merging into a top wall to define an open portion, said open portion having a length in the mesial-distal direction; and,
   b. a bracket component comprising a flange operable to be inserted into and retained within said housing, said flange extending through said open portion of said top wall to an archwire retention head for receiving and retaining therein an orthodontic archwire, said archwire retention head extending substantially the entire length of said open portion of said base component in said mesial-distal direction.

2. The orthodontic bracket assembly of claim 1, wherein said archwire retention head includes a tube having an archwire tunnel extending mesial-distally therethrough.

3. The orthodontic bracket assembly of claim 2, wherein the cross-sectional shape of said archwire tunnel is selected from the group consisting of rectangular, substantially square, and round.

4. The orthodontic bracket assembly of claim 2, wherein the cross-sectional shape of said archwire tunnel is oriented on a diagonal to enable an archwire to apply a torque to a tooth.

5. The orthodontic bracket assembly of claim 2, wherein the cross-sectional shape of said archwire tunnel corresponds to the cross-sectional shape of an orthodontic archwire to define a frictional fit.

6. The orthodontic bracket assembly of claim 2, wherein said archwire tunnel provides clearance with the archwire passing therethrough to reduce sliding friction between said orthodontic bracket assembly and the archwire.

7. The orthodontic bracket assembly of claim 2, wherein said archwire tunnel is square, each side being approximately 0.022 inches in length.

8. The orthodontic bracket assembly of claim 2, wherein said archwire tunnel is square, each side being approximately 0.018 inches in length.

9. The orthodontic bracket assembly of claim 1, wherein said archwire retention head is self-ligating.

10. The orthodontic bracket assembly of claim 1, wherein said archwire retention head includes a pair of opposed tie-wing portions.

11. The orthodontic bracket assembly of claim 1, wherein said housing includes a channel guide for receiving said flange of said bracket component within said housing.

12. The orthodontic bracket assembly of claim 11, wherein said channel guide is flared to facilitate entry of said flange within said housing.

13. The orthodontic bracket assembly of claim 11, wherein said flange has a substantially rectangular shape with two shorter sides and two longer sides and wherein the longer sides are configured to be located substantially parallel to said channel guide when said flange is retained within said housing.

14. The orthodontic bracket assembly of claim 13, wherein said channel guide extends mesially-distally.

15. The orthodontic bracket assembly of claim 11, wherein said flange has a substantially rectangular shape with two shorter sides and two longer sides and wherein said shorter sides are configured to be located substantially parallel to said channel guide when said flange is retained within said housing.

16. The orthodontic bracket assembly of claim 15, wherein said channel guide extends vertically and said flange is operable to slide within said channel guide from the occlusal surface to the gingival surface of a tooth.

17. The orthodontic bracket assembly of claim 1, wherein said base component is adapted for securement to a tooth by use of an adhesive material.

18. The orthodontic bracket assembly of claim 1, wherein said base component is arranged for attachment to a molar.

19. The orthodontic bracket assembly of claim 1, wherein said base component is arranged for attachment to an incisor, a canine, or a premolar tooth.

20. The orthodontic bracket assembly of claim 1, wherein said bracket component includes a neck extending between said flange and said archwire retention head, the shape and size of said neck being chosen to correct an in-out malocclusion of a tooth.

21. The orthodontic bracket assembly of claim 1, wherein said archwire retention head is positioned with respect to said flange in accordance with at least one dimensional parameter to correct the position of a maloccluded tooth.

22. The orthodontic bracket assembly of claim 21, wherein said at least one dimensional parameter is selected from the group consisting of tip, in-out offset, angulation, rotational offset, torque, and vertical.

23. The orthodontic bracket assembly of claim 1, wherein said archwire retention head includes a plurality of archwire tunnels.

24. The orthodontic bracket assembly of claim 1, wherein said archwire retention head is positioned on said flange at a predetermined angle to achieve a desired amount of angulation movement of the tooth to which the bracket assembly is secured.

* * * * *